United States Patent
Abdurahman et al.

(10) Patent No.: US 9,836,858 B2
(45) Date of Patent: Dec. 5, 2017

(54) METHOD FOR GENERATING A COMBINED PROJECTION IMAGE AND IMAGING DEVICE

(71) Applicant: SIEMENS AKTIENGESELLSCHAFT, Munich (DE)

(72) Inventors: Shiras Abdurahman, Erlangen (DE); Anna Jerebko, Hausen (DE); Michael Kelm, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 189 days.

(21) Appl. No.: 14/490,917

(22) Filed: Sep. 19, 2014

(65) Prior Publication Data

US 2016/0086356 A1  Mar. 24, 2016

(51) Int. Cl.
| | | |
|---|---|---|
| G06K 9/00 | (2006.01) | |
| G06T 11/00 | (2006.01) | |
| A61B 6/03 | (2006.01) | |
| A61B 6/00 | (2006.01) | |

(52) U.S. Cl.
CPC ........ *G06T 11/003* (2013.01); *A61B 6/032* (2013.01); *A61B 6/4078* (2013.01); *A61B 6/5205* (2013.01); *G06T 11/008* (2013.01); *G06T 2211/40* (2013.01); *G06T 2211/436* (2013.01)

(58) Field of Classification Search
CPC .......... G06T 11/003; G06T 11/008; G06T 2207/10112; G06T 2207/30068; G06T 2211/40; A61B 6/502; A61B 6/025
See application file for complete search history.

(56) References Cited

U.S. PATENT DOCUMENTS

| | | | | |
|---|---|---|---|---|
| 6,850,587 | B1 * | 2/2005 | Karimi | A61B 6/032 378/15 |
| 8,346,007 | B2 * | 1/2013 | Souza | G06T 5/002 345/419 |
| 2010/0246913 | A1 * | 9/2010 | Srinivas | A61B 6/025 382/131 |
| 2011/0038517 | A1 * | 2/2011 | Mistretta | A61B 6/02 382/128 |
| 2011/0317901 | A1 * | 12/2011 | Allmendinger | A61B 6/032 382/131 |

(Continued)

FOREIGN PATENT DOCUMENTS

| | | | | |
|---|---|---|---|---|
| DE | WO 2006109233 A2 * | 10/2006 | ........ | G06T 11/006 |
| WO | 2008012754 A2 | 1/2008 | | |

*Primary Examiner* — Bhavesh Mehta
*Assistant Examiner* — Ian Lemieux
(74) *Attorney, Agent, or Firm* — Laurence Greenberg; Werner Stemer; Ralph Locher (57) ABSTRACT

A method for generating a combined projection image from a medical inspection object, includes steps of capturing a set of initial projection images; reconstructing a first and a second three-dimensional volume from the set of initial projection images; generating a first re-projection image from the first three-dimensional volume and a second re-projection image from the second three-dimensional volume; weighting the first re-projection image and the second re-projection image; and combining the weighted first re-projection image and second re-projection image for generating the combined projection image.

13 Claims, 8 Drawing Sheets

(56) References Cited

U.S. PATENT DOCUMENTS

| | | | |
|---|---|---|---|
| 2012/0121064 A1* | 5/2012 | Bernard | G06T 11/008 378/37 |
| 2012/0189092 A1 | 7/2012 | Jerebko et al. | |
| 2012/0294502 A1* | 11/2012 | Chan | G06T 7/0012 382/131 |
| 2013/0136333 A1* | 5/2013 | Dennerlein | G06K 9/00 382/132 |
| 2014/0140599 A1* | 5/2014 | Kim | G06T 11/006 382/131 |

* cited by examiner

METHOD FOR GENERATING A COMBINED PROJECTION IMAGE AND IMAGING DEVICE

BACKGROUND OF THE INVENTION

Field of the Invention

The present invention relates to a method for generating a combined projection image (SM) from a medical inspection object and an imaging device for generating a combined projection image (SM) from a medical inspection object.

Computed tomography (CT), usually X-ray computed tomography, is a widely-used medical diagnostic tool, which allows the generation of tomographic images or slices of an area of interest in a patient. Radiologists often prefer using thick slab or thick-slice volume for diagnostic and screening reading. For example, 5.0 mm slabs are often used for clinical reading and data storage in thoracic CT, although thin, high resolution 0.5 mm slabs are available and used for computer applications such as three-dimensional volume rendering and computer aided diagnosis algorithms.

It is relatively easy to compute 3.0-5.0 mm slabs in thoracic CT images without losing diagnostically relevant information, for example by applying methods such as Average Intensity Projection (AIP) or Maximum Intensity Projection (MIP). The slab thickness is related to the combined thickness of the original slices in the volume. Generally, a slab is rendered as a two-dimensional image, so that the image can be printed or viewed on a computer screen.

In Digital Breast Tomosynthesis (DBT) data volumes are often reconstructed at a higher resolution, for example at a resolution of 85 microns for a slice thickness of 1.0 mm. Such a high-resolution volume allows visualization of the fine clinical details required for accurate medical diagnosis of breast cancer, for example microcalcifications of only 100 microns in size, very fine spiculations of masses, etc. A correct depiction of microcalcification morphology and spiculations is critical for the radiologist in order to be able to differentiate between benign and malignant lesions in breast tissue. This means that the amount of data in DBT volumes is very large. For example, the total volume of data for a single patient (e.g. including two DBT views and projection images) can exceed one gigabyte. The large data volume complicates data transfer and increases radiologist workload.

Another reason for generating slabs from the initial data is that a radiologist often needs to evaluate the distribution of an entire cluster of calcifications embedded in the surrounding tissue, including any masses and architectural distortions in that region.

In breast tissue, a lesion can often extend over 10.0 mm or more, and can extend in any random direction. Therefore, in order to be able to perform such an evaluation, a radiologist should be provided with very thick slabs, i.e. slabs with a thickness in excess of 10.0 mm. In some cases, it might be desirable to perform such an evaluation over the total volume (essentially the whole volume collapsed into a single slab). In the context of DBT such a single slab has also been called synthetic mammogram (SM) due to its similarity to conventional 2D mammograms.

SUMMARY OF THE INVENTION

It is an object of the present invention to produce a projection image from a medical object with high sharpness and contrast.

In a first aspect this object is solved by a method for generating a combined projection image from a medical inspection object, comprising the steps of capturing a set of initial projection images; reconstructing a first and a second three-dimensional volume from the set of initial projection images; generating a first re-projection image from the first three-dimensional volume and a second re-projection image from the second three-dimensional volume; weighting the first re-projection image and the second re-projection image; and combining the weighted first re-projection image and second re-projection image for generating the combined projection image. By the method the quality of the combined projection image is improved and noise is reduced. Diagnostically relevant information can be highlighted while image information with less relevance is down-weighed.

In a preferred embodiment of the method the first and/or second re-projection image is generated under an orthographic projection geometry, cone beam projection geometry or fan beam projection geometry from the first and/or second three-dimensional volume. In this embodiment geometries are employed that increase sharpness of the combined projection image.

In a further preferred embodiment of the method the first re-projection image and second re-projection image are linearly combined for generating the combined projection image. In this embodiment the combined projection image can be generated with few computational steps.

In a further preferred embodiment of the method reconstructing the first and second three-dimensional volume is based on a filtered back-projection algorithm. In this embodiment the three-dimensional volumes can be generated efficiently.

In a further preferred embodiment of the method the first or/and second three-dimensional volume are reconstructed from a reduced subset of initial projection images. In this embodiment an accumulation of artifacts can be avoided.

In a further preferred embodiment of the method the reduced subset of initial projection images comprises a number of initial projection images from view positions adjacent to the re-projection view position. In this embodiment a blurring is avoided to a great extent.

In a further preferred embodiment of the method the first and/or second re-projection image is generated by a maximum intensity projection, an average intensity projection or a highest-interest-projection from the first and/or second three-dimensional volume. In this embodiment projections are used that produce projection images with high contrast.

In a further preferred embodiment of the method capturing a set of initial projection images is based on x-ray imaging from different angles on a circular trajectory. In this embodiment initial images are captured from which the three-dimensional volumes can be constructed efficiently.

In a further preferred embodiment of the method capturing a set of initial projection images is based on a tomosynthesis acquisition. In this embodiment three-dimensional volumes can be reconstructed easily.

In a further preferred embodiment of the method the tomosynthesis acquisition is performed by a computer tomography apparatus. In this embodiment is well suited for investigating medical inspection objects.

In a further preferred embodiment of the method each pixel in the first re-projection image and the second re-projection is weighted independently. In this embodiment contrast and sharpness can be increased to a large extend.

In a further preferred embodiment of the method weighting is performed by multiplying the first and/or the second re-projection image with a weighting factor. In this embodiment weighting can be performed quick and with low complexity.

In a further preferred embodiment of the method the initial projection images, the reconstructed volumes, the re-projection images and/or the combined projection image are noise filtered. In this embodiment the quality of the resulting combined projection image is improved.

In a second aspect this object is solved by a method for generating a combined projection image from a medical inspection object, comprising the steps of capturing a set of initial projection images; reconstructing a three-dimensional volume from the set of initial projection images; generating a first re-projection image and a second re-projection image from the three-dimensional volume; weighting the first re-projection image and the second re-projection image; and combining the weighted first re-projection image and second re-projection image for generating the combined projection image. In this embodiment same advantages as in the method according to the first aspect are achieved.

In a third aspect this object is solved by an imaging device for generating a combined projection image from a medical inspection object, comprising a capturing means for capturing a set of initial projection images; a reconstruction means for reconstructing a first and a second three-dimensional volume from the set of initial projection images; a generation means for generating a first re-projection image from the first three-dimensional volume and a second re-projection image from the second three-dimensional volume; a weighting means for weighting the first re-projection image and the second re-projection image; and a combination means for combining the weighted first re-projection image and second re-projection image for generating the combined projection image. In this embodiment same advantages as in the method according to the first aspect are achieved.

Other features which are considered as characteristic for the invention are set forth in the appended claims.

Although the invention is illustrated and described herein as embodied in method for generating a combined projection image, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
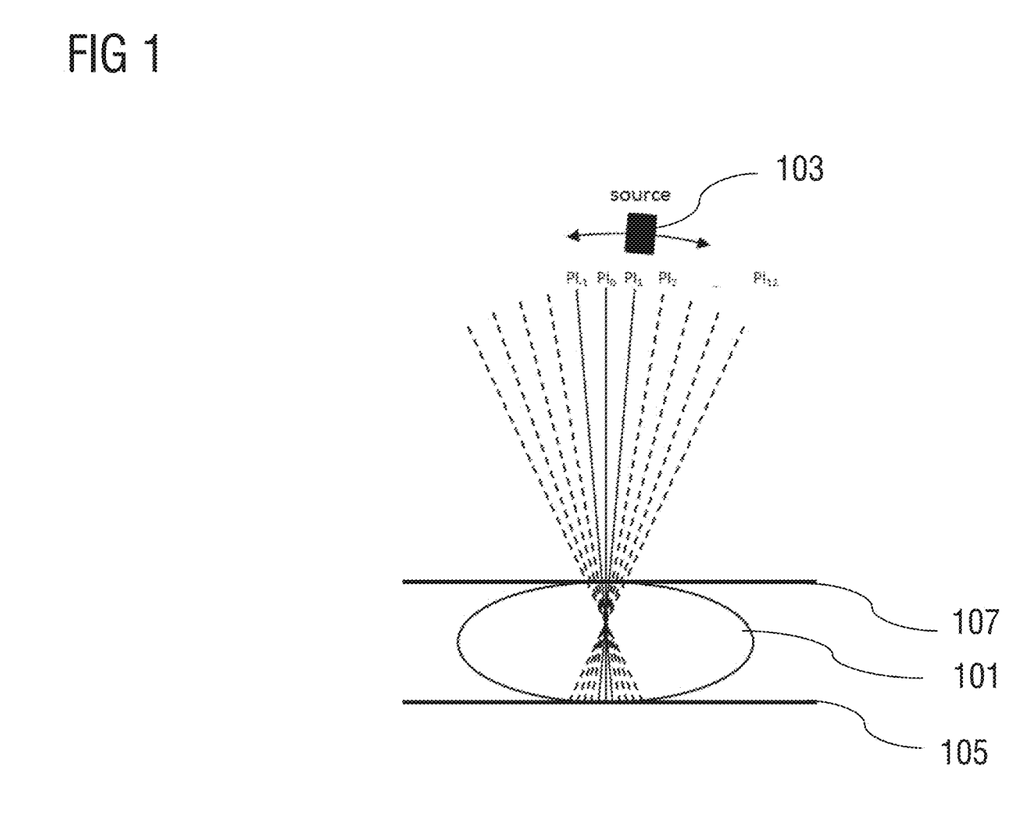
FIG. 1 shows a schematic view of a tomosynthesis acquisition.

FIG. 1 shows a schematic view of a tomosynthesis acquisition. The medical inspection object 101 (compressed breast) is imaged with x-ray from different angles on a circular trajectory. The breast is compressed by a compression paddle 107. X-Ray projection images of the medical inspection object 101 are captured by the x-ray detector 105.

The X-ray source 103 is moved on a circular path around the medical inspection object 101 in order to capture initial projection images PI from different projection directions by the x-ray detector 105. The x-ray detector 105 is positioned on the opposite side of the circle from the X-ray source 103.

X-ray computed tomography (x-ray CT) is a technology that uses computer-processed x-rays to produce tomographic images (virtual 'slices') of specific areas of the scanned object, allowing a user to see what is inside it without cutting it open.

Digital geometry processing is used to generate a three-dimensional volume of the inside of the medical inspection object 105 from a large series of two-dimensional radiographic initial projection images PI captured around a single axis of rotation. Medical imaging is a common application of x-ray CT. Its cross-sectional images are used for diagnostic and therapeutic purposes in various medical disciplines.

Figure 2:
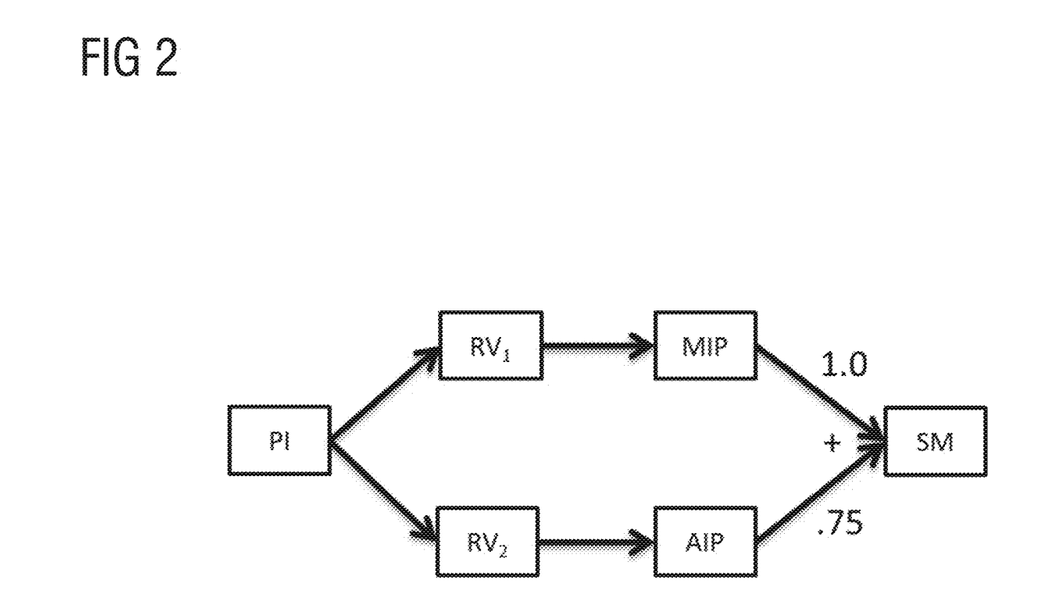
FIG. 2 shows a multiple projection synthetic mammogram example.

FIG. 2 shows a multiple projection synthetic mammogram example as a combined projection image SM. The three-dimensional volumes RV1 and RV2 are reconstructed from the initial projections images PI in this example, e.g. by means of a microprocessor. While both reconstructed three-dimensional volumes RV1 and RV2 are done with the same kind of filtered back-projection (FBP) algorithm, the reconstructed volume RV1 is based on 25 projections and the reconstructed volume RV2 is based on a subset of only 3 central projections. The central projection directions as a subset from all projection directions are drawn with solid lines in FIG. 1. While the reconstructed volume RV2 from the central projections is expected to exhibit more noise and more severe out-of-plane artifacts, the angles at which these artifacts occur are narrower. This causes less blurring from the out-of-plane artifacts, when re-projecting these volumes.

The processed initial tomosynthesis projection images are transformed in a single re-projected image RP on the basis of single reconstructed volume RV.

Figure 3:
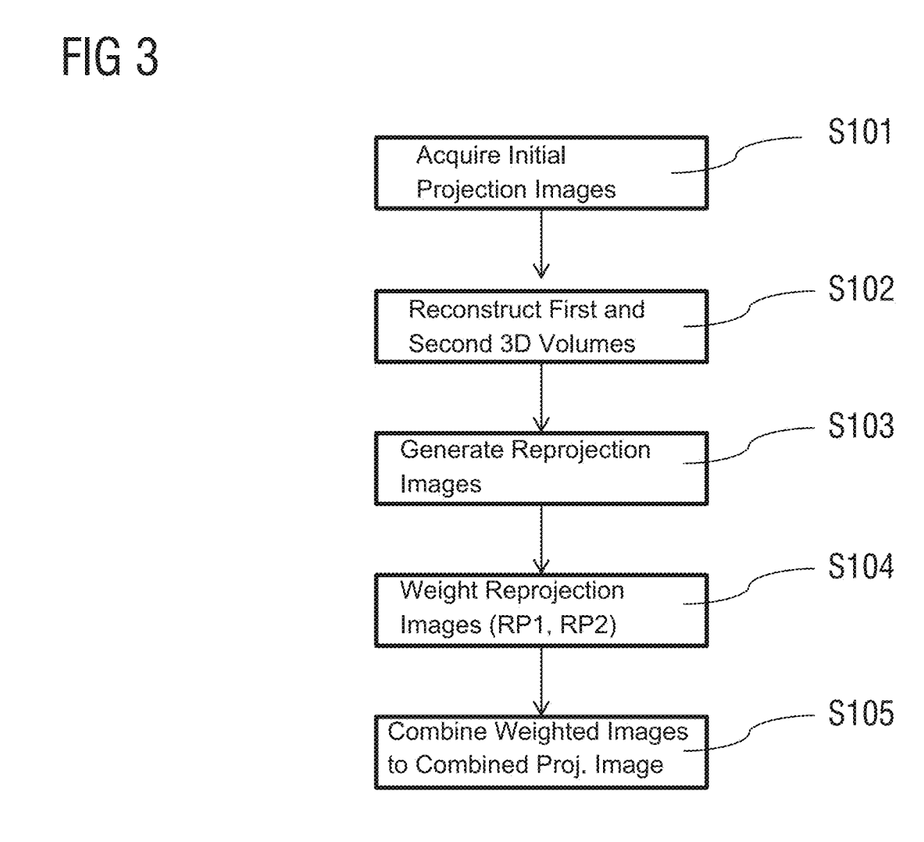
FIG. 3 shows a diagram of method steps.

FIG. 3 shows a diagram of method steps for generating a combined projection image SM from a medical inspection object 101. In step S101 a set of initial projection images PI is captured by the tomosynthesis acquisition. Capturing is can be done for example with a solid state X-ray detector.

In step S102 at least a first and a second three-dimensional volume RV1, RV2 are reconstructed from the set of initial projection images PI, e.g. by a means of a computer algorithm. Reconstructing essentially involves solving the inverse Radon transformation on the basis of the captured initial projection images.

Then in step S103 at least a first re-projection image RP1 is generated from the first three-dimensional volume RV1 and at least a second re-projection image RP2 is generated from the second three-dimensional volume RV2. Generating re-projection images can be performed by summing pixels on a virtual projection beam considering a particular geometry, like a cone beam.

In step S104 the first re-projection image RP1 and the second re-projection image RP2 are weighted. Weighting can be done either by independently weighting each pixel in the re-projection images RP1 and RP2 or by multiplying each of the entire re-projection images RP1 and RP2 with a weighting factor.

Finally in step S105 the weighted first re-projection image RP1 and second re-projection image RP2 is combined, e.g. added or subtracted, for generating the combined projection image (SM).

Figure 4:
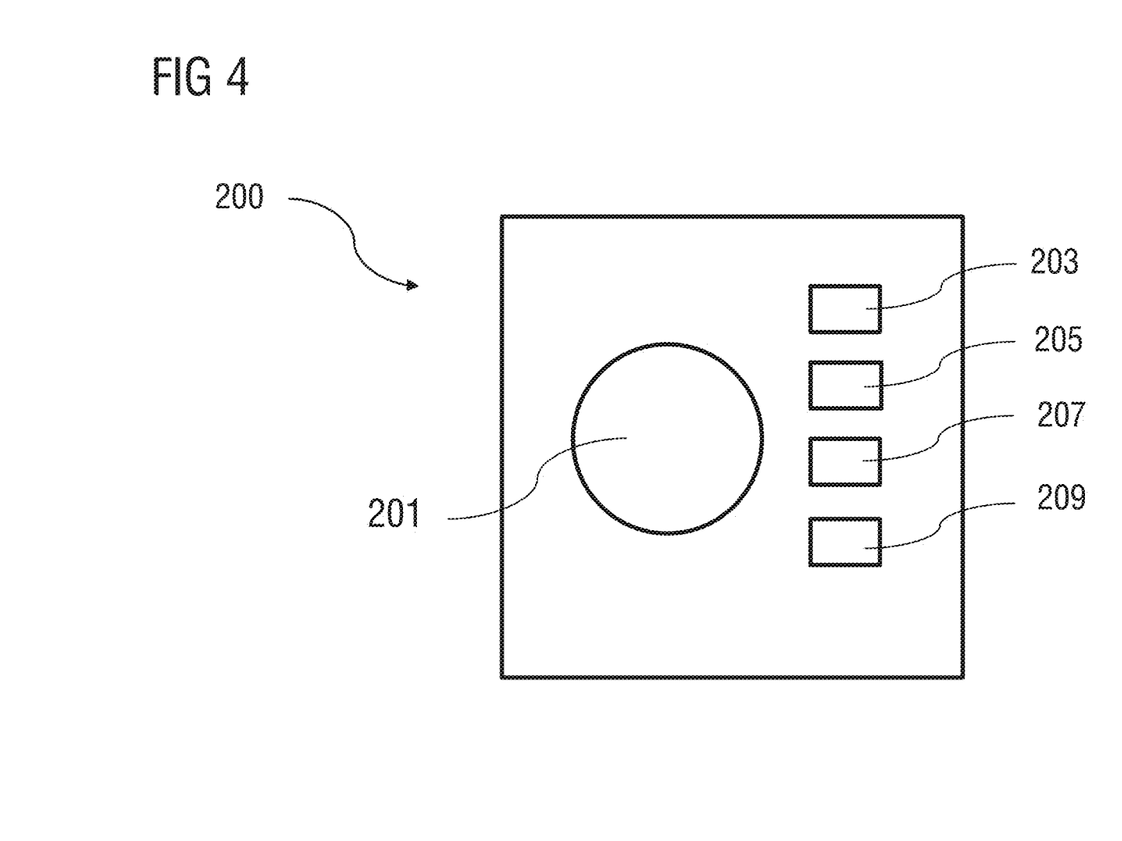
FIG. 4 shows an imaging device.

FIG. 4 shows an imaging device 200 for generating the combined projection image SM from the medical inspection object 101. The imaging device 200 is for example a computer tomography apparatus. The imaging device comprises a capturing means 201 for capturing a set of initial projection images PI, e.g. an x-ray detector 105. A reconstruction means 203 serves for reconstructing at least a first and at least a second three-dimensional volume RV1, RV2 from the set of initial projection images PI by a mathematical calculation. A generation means 205 serves for generating at least a first re-projection image RP1 from the first three-dimensional volume RV1 and at least a second re-projection image RP2 from the second three-dimensional volume RV2 by a calculated re-projection. A weighting means 207 for weighting the first re-projection image RP1 and the second re-projection image RP2. Finally the imaging device 200 comprises a combination means 209 for combining the weighted first re-projection image RP1 and second re-projection image RP2 for generating the combined projection image SM.

The reconstruction means 203, the generation means 205, the weighting means 207 and the combination means 209 can be implemented by a computer with a microprocessor and a data storage that is capable of processing the captured initial projection images PI.

Figure 5:
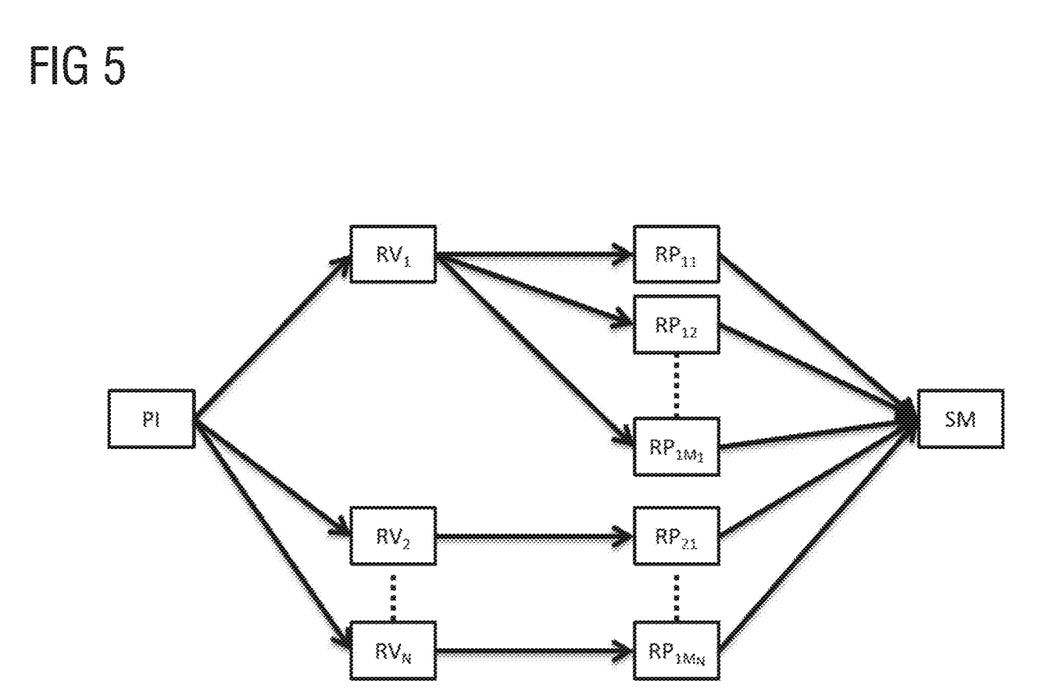
FIG. 5 shows a principle of multiple projection synthetic mammogram.

FIG. 5 shows a principle of a multiple projection synthetic mammogram as a combined projection image. PI denotes initial projection images, RV denotes reconstructed volumes, RP denotes re-projection images, and SM denotes a combined projection image, like the synthetic mammogram.

From the initial projection images PI captured by the detector 105 $n$ three-dimensional volumes $RV_1 \ldots RV_n$ are reconstructed. Thus n reconstructed volumes $RV_1 \ldots RV_n$ with n>0 are given. From the $n^{th}$ reconstructed volume $RV_n$ m two-dimensional projection images $RP_{mn}$ on the same virtual detector are computed. The projections of the projection images $RP_{mn}$ may vary in type, e.g., Maximum-Intensity-Projection (MIP), Average-Intensity-Projection (AIP) and Highest-Interest-Projection (HIP) as well as projection geometry, e.g. orthographic, cone beam or fan beam.

The synthetic mammogram SM as combined projection image is computed as linear combination of the re-projection images $RP_{mn}$, for example by:

$$SM(u,v) = \sum_{n=1}^{N} \sum_{m=1}^{M_n} w(m,n,u,v) \cdot RP_{mn}(u,v), \quad (1)$$

where N>0, $\sum_{n=1}^{N} M_n > 1$ and w(m,n,u,v)≥0.

This produces a weighted linear combination of multiple re-projection images RP, in which the weights can be chosen independently for each pixel in each projection image. The re-projection images RP can be obtained from one or more reconstructed three-dimensional volumes RV.

Instead of the linear combination described in Eq. (1), other ways of combining/mixing of re-projection images are conceivable. In addition filtering of the initial projection images PI, the reconstructed volumes RV, the re-projection images RP and/or the combined projection image SM can improve the final result.

Multiple projections and/or multiple reconstructions can be used to synthesize a 2D mammogram as a combined projection image. In particular, advantages from different projections and reconstructions can be exploited to generate a synthetic mammogram that highlights diagnostically relevant features. Reconstructing the three dimensional volume RV from a subset of initial projections PI avoids accumulating artifacts when re-projecting.

Figure 6:
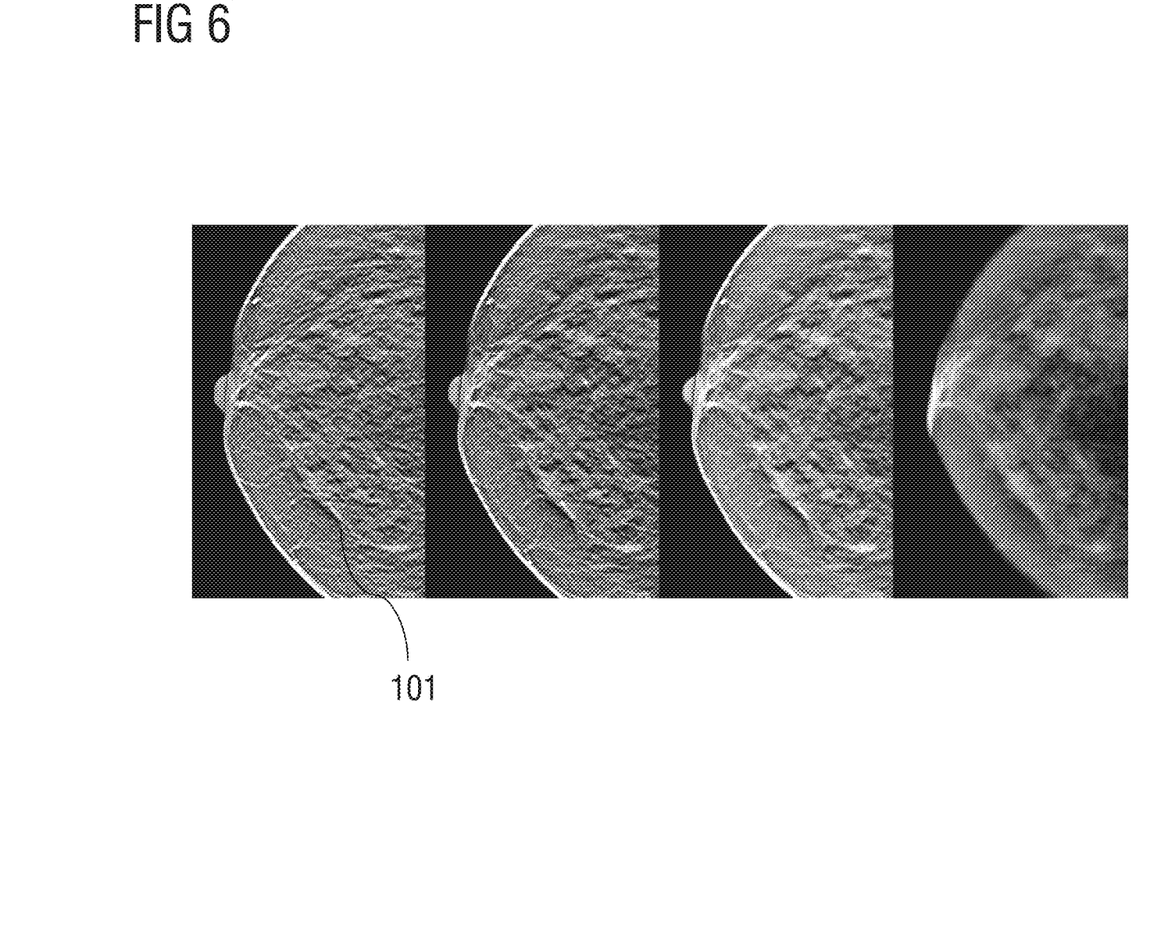
FIG. 6 shows AIP projections of a reconstructed volume.

FIG. 6 shows examples for Average Intensity Projections (AIPs) from a reconstructed volume RV which has been reconstructed using 1, 3, 5 and all 25 projections respectively (from left to right). The medical inspection object 101 is a human breast.

While the contrast-to-noise ratio improves with the number of projection images PI, structures tend to get more and more blurred. While the image noise decreases from left to right, the images also get increasingly blurred.

A similar tendency can be seen for the Maximum-Intensity-Projections (MIPs) in FIG. 5. Due to the different noise behavior of AIPs and MIPs, however, for a MIP preferably a volume reconstructed with all projections is used, while for the AIP, a volume reconstructed with a subset of less projections, for example 3, is preferred.

The different kind of projections, such as MIP and AIP but also different Highest-Interest-Projections (HIP) are well-suited for highlighting particular diagnostically relevant structures. In particular, these projections exhibit differences regarding contrast-to-noise ratio and spatial noise homogeneity.

However, different three-dimensional reconstructions RV with varying contrast, noise and artifact-behavior can also be constructed from the initial projection images PI. Differences may come from using different reconstruction algorithms (e.g. FBP—filtered back projection or IR—iterative reconstruction) or from different parameterizations (e.g. usage of different backprojection filters in FBP or different regularizers in IR).

Figure 7:
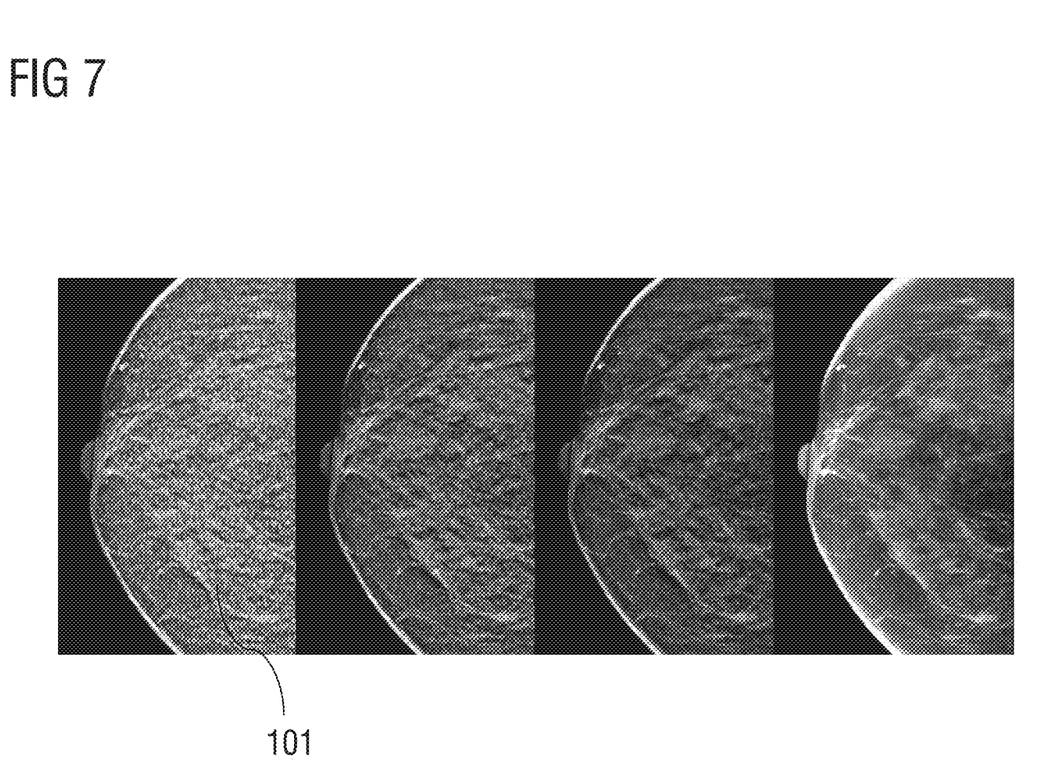
FIG. 7 shows MIP projections of a reconstructed volume.

FIG. 7 shows MIPs of a volume with 1, 3, 5, and 25 projections (from left to right). While the image noise decreases from left to right, the images also get increasingly blurred.

Figure 8:
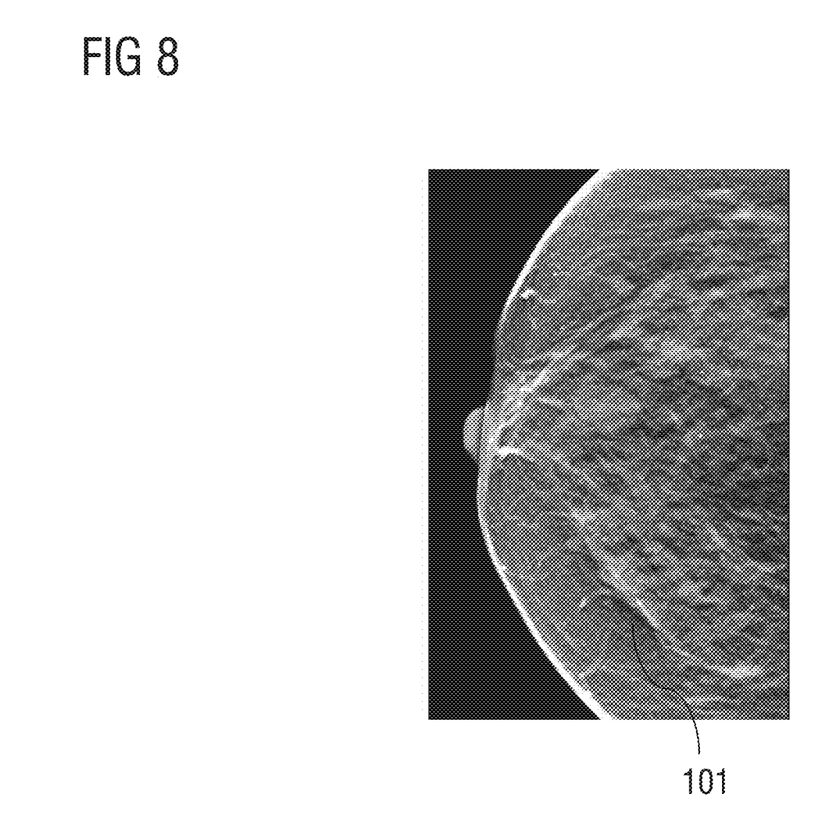
FIG. 8 shows a synthetic mammogram.

FIG. 8 shows a synthetic mammogram on the basis of a weighted MIP (weighting factor: 1) from a reconstructed volume RV with 25 projections and a weighted AIP (weighting facto. 0.75) from a reconstructed volume RV with 3 projections. Mixing the re-projection images RP leads to sharper combined projection images SM with more details.

The scope of the invention is defined by the claims and is not restricted by special features discussed in the description or shown in the figures. All features discussed with respect to different embodiments can be combined variously and independently in order to simultaneously realize their technical effect.

The following is a summary list of reference numerals and the corresponding structure used in the above description of the invention:

101 medical inspection object
103 x-ray source
105 detector
107 compression paddle
200 imaging device
201 capturing means
203 reconstruction means
205 generation means
207 weighting means
209 combination means
PI initial projection images
RV reconstructed three-dimensional volume
RP re-projection image
SM combined projection image/synthetic mammogram

The invention claimed is:

1. A method of generating a combined projection image from a medical inspection object, the method comprising the steps of:
capturing a set of initial projection images;
reconstructing a first three-dimensional volume and a second three-dimensional volume from the set of initial projection images;
generating a first re-projection image from the first three-dimensional volume and a second re-projection image from the second three-dimensional volume;
weighting the first re-projection image and the second re-projection image; and
generating a single combined projection image by linearly combining the weighted first re-projection image and the weighted second re-projection image, wherein the first re-projection image is a Maximum-Intensity-Projection (MIP) and the second re-projection image is an Average-Intensity Projection (AIP).

2. The method according to claim 1, which comprises generating one or both of the first and second re-projection images under an orthographic projection geometry, cone beam projection geometry or fan beam projection geometry from the respective first or second three-dimensional volume.

3. The method according to claim 1, wherein the step of reconstructing the first and second three-dimensional volume is based on a filtered back-projection algorithm.

4. The method according to claim 1, which comprises reconstructing the first or/and the second three-dimensional volume from a reduced subset of initial projection images.

5. The method according to claim 4, wherein the reduced subset of initial projection images comprises a number of initial projection images from views adjacent to views used to reconstruct one of the first and second re-projection images.

6. The method according to claim 1, wherein the step of capturing a set of initial projection images is based on x-ray imaging from different angles on a circular trajectory.

7. The method according to claim 1, wherein the capturing step comprises acquiring a set of initial projection images based on a tomosynthesis acquisition.

8. The method according to claim 7, which comprises performing the tomosynthesis acquisition with a computer tomography apparatus.

9. The method according to claim 1, which comprises independently weighting each pixel in the first re-projection image and in the second re-projection.

10. The method according to claim 1, wherein the weighting step comprises multiplying the respective first and/or second re-projection image with a weighting factor.

11. The method according to claim 1, which comprises noise filtering at least one or more of the initial projection images, the reconstructed volumes, the re-projection images, and/or the combined projection image.

12. A method for generating a combined projection image from a medical inspection object, the method comprising the steps of:
capturing a set of initial projection images;
reconstructing a three-dimensional volume from the set of initial projection images;
generating a first re-projection image and a second re-projection image from the three-dimensional volume;
weighting the first re-projection image to form a weighted first re-projection image and the second re-projection image to form a weighted second re-projection image; and
generating a single combined projection image by linearly combining the weighted first re-projection image and the weighted second re-projection image, wherein the first re-projection image is a Maximum-Intensity-Projection (MIP) and the second re-projection image is an Average-Intensity Projection (AIP).

13. An imaging device for generating a combined projection image from a medical inspection object, the device comprising:
a capturing device for capturing a set of initial projection images;
reconstruction means for reconstructing a first and a second three-dimensional volume from the set of initial projection images;
generation means for generating a first re-projection image from the first three-dimensional volume and a second re-projection image from the second three-dimensional volume;
weighting means for weighting the first re-projection image and the second re-projection image; and
combination means generating a single combined projection image by linearly combining the weighted first re-projection image and the weighted second re-projection image, wherein the first re-projection image is a Maximum-Intensity-Projection (MIP) and the second re-projection image is an Average-Intensity Projection (AIP).

* * * * *